United States Patent
Yang et al.

(10) Patent No.: US 9,115,042 B2
(45) Date of Patent: Aug. 25, 2015

(54) METHOD FOR PREPARING 2,3,3,3-TETRAFLUOROPROPENE

(75) Inventors: Gang Yang, Shaanxi (CN); Lei Xu, Shaanxi (CN); Huie Yang, Shaanxi (CN); En Jiang, Shaanxi (CN); Jianping Fan, Shaanxi (CN); Xintang Zhao, Shaanxi (CN); Changhua Zeng, Shaanxi (CN); Wenqing Zhang, Shaanxi (CN); Yunlong Lei, Shaanxi (CN); Zhong Li, Shaanxi (CN); Shukang Chen, Shaanxi (CN)

(73) Assignees: SINOCHEM LANTIAN CO., LTD., Zhejiang (CN); SINOCHEM MODERN ENVIRONMENTAL PROTECTION CHEMICALS (XI'AN) CO., LTD., Xi'an, Shaanxi (CN)

( * ) Notice: Subject to any disclaimer, the term of this patent is extended or adjusted under 35 U.S.C. 154(b) by 0 days.

(21) Appl. No.: 14/344,582

(22) PCT Filed: Sep. 11, 2012

(86) PCT No.: PCT/CN2012/081238
§ 371 (c)(1),
(2), (4) Date: Mar. 12, 2014

(87) PCT Pub. No.: WO2013/037286
PCT Pub. Date: Mar. 21, 2013

(65) Prior Publication Data
US 2014/0350312 A1 Nov. 27, 2014

(30) Foreign Application Priority Data
Sep. 14, 2011 (CN) .......................... 2011 1 0270856

(51) Int. Cl.
| C07C 17/20 | (2006.01) |
| B01J 27/132 | (2006.01) |
| B01J 23/00 | (2006.01) |
| B01J 23/26 | (2006.01) |
| B01J 37/00 | (2006.01) |

(52) U.S. Cl.
CPC ............. *C07C 17/206* (2013.01); *B01J 23/002* (2013.01); *B01J 23/26* (2013.01); *B01J 27/132* (2013.01); *B01J 37/0018* (2013.01); *B01J 2523/00* (2013.01)

(58) Field of Classification Search
CPC ..... C07C 17/206; B01J 27/132; B01J 23/002; B01J 23/26; B01J 37/0018; B01J 2523/00
USPC .......... 502/224, 228, 300, 306, 307; 423/464, 423/593; 570/156, 160
See application file for complete search history.

(56) References Cited

U.S. PATENT DOCUMENTS

| 2,931,840 A | 4/1960 | Marquis |
| 2,996,555 A | 8/1961 | Rausch |
| 6,165,931 A | 12/2000 | Rao |
| 2007/0197842 A1 | 8/2007 | Mukhopadhyay et al. |
| 2009/0253946 A1 | 10/2009 | Van Der Puy |
| 2009/0299107 A1 | 12/2009 | Wang et al. |
| 2011/0124930 A1* | 5/2011 | Smith et al. .................... 570/156 |
| 2011/0160497 A1 | 6/2011 | Deur-Bert et al. |
| 2014/0121424 A1* | 5/2014 | Nose et al. ..................... 570/160 |

FOREIGN PATENT DOCUMENTS

| CA | 690037 A | 7/1964 |
| CN | 1408476 A | 4/2003 |
| CN | 101535227 A | 9/2009 |
| CN | 102099319 A | 6/2011 |
| JP | H06-228022 A | 8/1994 |
| JP | 3374426 B2 | 2/2003 |
| JP | 2011-517681 A | 6/2011 |
| WO | 2006/063069 A2 | 6/2006 |
| WO | 2007/019355 A1 | 2/2007 |
| WO | 2007/117391 A1 | 10/2007 |
| WO | 2008/002500 A1 | 1/2008 |
| WO | 2008/030440 A2 | 3/2008 |
| WO | 2008/030443 A1 | 3/2008 |
| WO | 2008/054778 A2 | 5/2008 |
| WO | 2008/054779 A1 | 5/2008 |
| WO | 2008/054780 A2 | 5/2008 |
| WO | 2008/060614 A2 | 5/2008 |
| WO | 2009/084703 A1 | 7/2009 |
| WO | 2010/059493 A1 | 5/2010 |
| WO | 2010/123154 A2 | 10/2010 |

OTHER PUBLICATIONS

International Search Report issued in PCT/CN2012/081238 mailed on Dec. 20, 2012 (8 pages).
EPO Communication and Extended European Search Report dated Apr. 8, 2015, issued by the European Patent Office, The Hague, in corresponding European Patent Application No. EP-12832451.4 (8 pages).
Wenzhi, Jia, et al., "Fluorination of dichlorodifluoromethane to synthesize tetrafluoromethane over Cr2O3-AlF3 catalyst"; Journal of Industrial and Engineering Chemistry, vol. 17, May 13, 2011; XP55179427; pp. 615-620.
Notice of Reasons for Rejection (Office Action) dated Apr. 20, 2015, issued by the Japan Patent Office in corresponding Japanese Patent Application No. JP 2014-530086, with Google machine-translation (7 pages).

* cited by examiner

*Primary Examiner* — Shailendra Kumar
(74) *Attorney, Agent, or Firm* — Osha Liang LLP

(57) ABSTRACT

Provided are a fluorination catalyst for preparing 2,3,3,3-tetrafluoropropene and a method using the catalyst for preparing 2,3,3,3-tetrafluoropropene. The catalyst has the following structural formula: $Cr_x(Y,Z)_{0.005-0.5}O_{0.1-1.0}F_{1.0-3.0}$, where Y is one or a combination of two or more among Al, Zn, and Mg, and where Z is a rare earth element having an oxygen-storing/releasing function. The catalyst has in preparing 2,3,3,3-tetrafluoropropene the advantages of increased raw material conversion rate, great product selectivity, and extended catalyst service life.

18 Claims, No Drawings

METHOD FOR PREPARING 2,3,3,3-TETRAFLUOROPROPENE

This application is a 371 of PCT/CN2012/081238, filed on Sep. 11, 2012.

TECHNICAL FIELD

This invention relates to a method for the preparation of fluoroalkenes, particularly 2,3,3,3-tetrafluoropropene.

BACKGROUND TECHNOLOGY

According to the Montreal Protocol on Substances that Deplete the Ozone Layer, the currently most widely used fluoroalkane, HFC-134a, which also has the most greenhouse effects (its GWP values is 1340, relative to $CO_2$), would be gradually eliminated. In the search for substitutes for FHC-134a, 2,3,3,3-tetrafluoropropene (HFO-1234yf) has been accepted by major European automakers as a substitute for HFC-134a. In Europe, U.S. and Japan, HFO-1234yf has been approved for sale starting from Jan. 1, 2011. This compound will be used on new cars as a substitute for the third generation coolant, HFC-1234a. By Jan. 1, 2017, no automobile is allowed to use HFC-1234a. HFO-1234yf is also a monomer or co-polymer starting material for the synthesis of thermally stable and highly flexible rubber material; it has a great market potential.

Synthetic routes for HFO-1234yf are limited to the following reported processes:

- Canadian Patent No. 690037 and U.S. Pat. No. 2,931,840 reported the synthesis of 2,3,3,3-tetrafluoropropene by high temperature cracking using chloromethane ($CH_3Cl$) and tetrafluoroethylene ($CF_2=CF_2$), or chloromethane and difluorochloromethane (R22), as the starting materials.
- U.S. Patent Application Publication No. 2009/253946 A1 reported a method for the synthesis of HFO-1234yf by high temperature cracking of chloromethane and trifluorochloroethylene ($CF_2=CFCl$). This method produce substantial amounts of impurities and the yield is low.
- U.S. Pat. No. 2,996,555 reported a method for the synthesis of HFO-1234yf using $CX_3CF_2CH_3$ (X=Br, Cl, or F) as a starting material.
- PCT Publication No. WO 2007/019355 reported a method for the synthesis of both HFO-1234yf and HFC-1234ze starting from $CX_3CCl=CClY$ (X and Y are independently selected from F or Cl).
- PCT Publication No. WO 2007/117391 reported a method that uses $CHF_2CHFCHF_2$ (HFC-236ea) and $CF_3CHFCH_2F$ (HFC-245eb) to produce both HFC-1225ye and HFO-1234yf.
- PCT Publication Nos. WO 2008/002500 and WO 2008/030440 reported a method using $CF_3CF=CFH$ (HFC-1225ye) as a starting material to synthesize HFO-1234yf.
- PCT Publication No. WO 2008/054780 reported a method using $CCl_3CF_2CF_3$ (CFC-215cb) or $CCl_2FCF_2CClF_2$ (CFC-215ca) as a starting material to react with $H_2$ under the catalysis of a catalyst to synthesize a product containing HFO-1234yf.
- PCT Publication Nos. WO 2008/054779 and WO 2008/060614 reported a method for the synthesis of HFO-1234yf using $CHCl_2CF_2CF_3$ (HFC-225ca) or $CHClFCF_2CClF_2$ (HCFC-225cb) as a starting material.
- PCT Publication Nos. WO 2008/054778 reported a method for the synthesis of HFO-1234yf by hydrogenation of $CHCl_2CF_2CF_3$ (HFC-225ca).
- PCT Publication Nos. WO 2008/0443 reported a method for the synthesis of HFO-1234yf by catalytic isomerization of HFC-1234ze.
- U.S. Patent Application Publication No. 2009/299107 reported a method for the synthesis of HFO-1234yf using $CF_3CFClCH_3$ (HFC-244bb) as a starting material.
- U.S. Patent Application Publication No. 2007/197842 reported a method for the synthesis of HFO-1234yf in three steps starting using $CCl_2=CClCH_2Cl$ as a starting material.
- PCT Publication Nos. WO 2009/084703 reported a method for the synthesis of HFO-1234yf using $CF_3CF=CF_2$ (HFP) as a starting material.
- PCT Publication Nos. WO 2006/063069 reported a method for the synthesis of HFO-1234yf by dehydrating a starting material, 2,2,3,3,3,-pentafluoropropan-1-ol ($CF_3CF_2CH_2OH$).

Among these reported methods, the one using HCFC-1233xf as the starting material for the synthesis of HFO-1234yf represents most commercial values.

U.S. Patent Application Publication No. 2011/0160497 discloses a reaction that uses a chromium-containing fluorination catalyst and 0.1%-0.15% $O_2$ based on the moles of HCFC-1233xf. However, the conversion rate of HCFC-1233xf reaches only about 10%. HFO-1234yf selectivity can reach 72.5%. PCT publication No. WO 2010/123154 A1 discloses a method that controls the chromium valance in the catalyst $CrO_m$ (1.5<m<3.0), i.e., by introducing 0.1-1.0 mole $O_2$/mole HCFC-1233xf to control the valance of chromium. The reaction results show that the conversion rate of HCFC-1233xf can reach 37.8%, and the selectivity of HFO-1234yf can reach 75.2%. In these two methods, the high valance chromium is not stable and is prone to convert to the low valance chromium, leading to short life of the catalyst and the catalyst activity degrades relative fast.

SUMMARY OF THE INVENTION

An objective of the present invention is to provide a catalyst for the preparation of 2,3,3,3-tetrafluoropropene and a method for the preparation of 2,3,3,3-tetrafluoropropene using 2-chloro-3,3,3-trifluoropropene as a starting material. Embodiments of the invention have the advantages of high rates of conversion of the starting material, high selectivities of product formation, long lives of the catalysts, etc.

To achieve the objective of the invention, the present invention includes the following embodiments:

A catalyst for the preparation of 2,3,3,3,-tetrafluoropropene, characterized in that the catalysis has the following formula (I):

$$Cr_1(Y,Z)O_{0.005-0.5}O_{0.1-1.0}F_{1.0-3.0} \quad (I)$$

wherein Y is selected from one, or a combination of two or more, of Al, Zn, or Mg; and Z is a rare earth capable of storing and releasing oxygen.

Rare earth elements include Sc, Y, and the lanthanide series: La, Ce, Pr, Nd, Pm, Sm, Eu, Gd, Tb, Dy, Ho, Er, Tm, Yb, Lu, for a total of 17 elements. The rare earth elements for use in embodiments of the invention are those capable of storing and releasing oxygen. A typical rare earth element capable of storing and releasing oxygen is Ce, La, or Pr. In accordance with preferred embodiments of the invention, a rare earth element capable of storing and releasing oxygen is one, or a combination of two or more, of Ce, La, or Pr.

In accordance with preferred embodiments of the invention, in the preparation of a fluorination catalyst of the invention, a fluorine containing surfactant is preferably added. Fluorine containing surfactants preferably are perfluoro-1-octylsulfonyl fluoride (POSF) or a soluble slat of perfluorooctylsulfonic acid (POSA). Preferred soluble slats of perfluorooctylsulfonic acid include sodium perfluorooctylsulfonate and potassium perfluorooctylsulfonate.

In the above-described embodiments of the invention, the catalyst comprises a multi-metal base as a major component, supplemented with an auxiliary component that comprises a rare earth element capable of storing and releasing oxygen, wherein the multi-metal base comprises chromium and one selected from Al, Zn, Mg or a combination thereof. A fluorine-containing surfactant is added in the preparation of the catalyst, and the precursor of the catalyst is calcined at 200-400° C. in an atmosphere of air and $N_2$ mixed gas.

In accordance with embodiments of the invention, the physical state of the catalyst is not critical. The catalyst may be in a shape of balls, flakes, or granules. The catalyst is preferably pretreated with HF, although this is not an essential step. The pretreatment with HF can convert the oxides on the catalyst surface into fluorides. This pretreatment step may be performed with the catalyst and HF in an appropriate catalyst reactor, which may be accomplished by passing anhydrous HF at a selected temperature, such as about 200-500° C., through the catalyst for 15-400 minutes.

Some embodiments of the invention relate to methods for the preparation of 2,3,3,3-tetrafluoropropene. A method of the invention uses 2-chloro-3,3,3-trifluoropropene as a starting material, under the catalysis of a fluorination catalyst having the above described formula (I), in the presence of $O_2$ and/or $O_3$, to react with anhydrous hydrogen fluoride (HF) to synthesize 2,3,3,3,-tetrafluoropropene.

In embodiments of the invention, a molar ratio of the anhydrous hydrogen fluoride and 2-chloro-3,3,3,-trifluoropropene preferably is 3-20:1, more preferably 5-10:1.

In embodiments of the invention, when $O_2$ is used alone, a molar ratio of $O_2$ and 2-chloro-3,3,3-trifluoropropene is preferably 1-3:1, more preferably 1-2:1. When O3 is used alone, a molar ratio of O3 and 2-chloro-3,3,3-trifluoropropene is preferably 0.1-2:1, more preferably 0.1-1:1.

In accordance with embodiments of the invention, the starting material 2-chloro-3,3,3,-trifluoropropene is preferably preheated prior to the reaction. The temperature for preheating is preferably 100-500° C., more preferably 100-350° C.

In accordance with embodiments of the invention, the temperature for the fluorination reaction is preferably 200-500° C., more preferably 300-450° C. The reaction time (contact time) is preferably 1-300 seconds, more preferably 10-150 seconds. The reaction may be conducted under a pressure lower than the atmospheric pressure, under the ambient pressure, or under a higher pressure, preferably the reaction conducted under a high pressure of 0.1-1.2 MPa.

Embodiments of the invention relate to methods for the preparation of 2,3,3,3-tetrafluoropropene. A method of the invention may include the following steps:
(1) Add a fluorination catalyst of formula (I) into a reactor;
(2) Mix the starting material 2-chloro-3,3,3-trifluoropropene, anhydrous hydrogen fluoride, and $O_2$ and/or $O_3$ well and then add the mixture into a preheating reactor to preheat the mixture, followed by introduction into a gasification reactor to gasify the reaction mixture, which is then introduced into the reactor to carry out the reaction. The preheating temperature is 100-500° C. and the reaction temperature is 200-500° C.;
(3) Introduce the reaction product into a first separation tower, wherein the reaction product contains the starting material 2-chloro-3,3,3-trifluoropropene, anhydrous hydrogen fluoride, and $O_2$ and/or $O_3$. Separate $O_2$ and/or $O_3$ and HCl stream from the top of the first separation tower. After washing with water to remove HCl, the $O_2$ and/or $O_3$ stream is discharged into the atmosphere or passed to a recovery apparatus for recovery. The stream remaining in the reactor, which contains HCFC-1233xf, HFO-1234yf, and HF, is introduced into a second separation tower to continue the separation;
(4) Separate a stream containing the HFO-1234yf crude product from the second separation tower. The HFO-1234yf crude product can be purified to give the final product;
(5) The stream remaining at the bottom of the second separation tower is recycled back into the reactor to continue the reaction.

The reactors, distillation towers and other related starting material delivery pipes/tubes, discharge pipes/tubes, and other related elements used in embodiments of the invention should be made of a corrosion resistant material. Typical corrosion resistant materials include nickel alloys, stainless steel, copper-plated steel, etc.

Compared with prior art methods, embodiments of the invention, by adding rare earth elements capable of storing and releasing oxygen to the catalysts and by introducing more oxygen or the higher oxidation potential $O_3$ into the reactions, greatly increase the conversion of HCFC-1233xf, with a conversion rate up to 69.8%, and with a slightly lower HFO-1234yf selectivity, up to 94%, while the useable lives of the catalysts are lengthened.

EXAMPLES

The invention will be further illustrated with specific examples. However, the invention is not limited by these specific examples. One skilled in the art would appreciate that the invention encompasses the scopes of the claims, as well as all alternatives, improvements, and equivalent embodiments.

Example 1

Preparation of the Catalysts

Dissolve 60 g $Cr(NO_3)_3 \cdot 9H_2O$ and 0.05 g $La(NO_3)_3 \cdot 6H_2O$ in 2,000 ml deionized water to make a mixed salt solution. Put the mixed salt solution in a three-neck flask and warmed to 40° C. on a water bath. Add dropwise 150 g of 5% (wt) ammonia water solution. Control the pH of the final solution at 7-9 and continue stirring for 1 h. The solution is then allowed to sit at room temperature to age. Collect the precipitates by filtration and wash the precipitates with deionized water until pH neutral. The precipitates are dried at 110° C. for 16 hrs to afford the catalyst precursor.

The catalyst precursor is pressed into tablets, which are then placed in a reactor and calcined at 400° C. for 2 hours in an atmosphere of $N_2$ and air mixed gas. Then, a mixed gas if N2 and HF are introduced into the reactor to fluorinate the catalysts at 350° C. for 3 hours, resulting in the production of fluorinated catalysts.

Example 2

Preparation of HFO-1234yf

In a Monel alloy tube (25 mm diameter), fill with the fluorinated catalyst prepared in Example 1. The amount of the catalyst filled in the tube is 50 ml. Preheat a mixture of anhydrous HF, HCFC-1233xf, and $O_2$ (in a molar ratio of 15:1:1) in the preheating can to a temperature of 300° C. Then, introduce the preheated mixture into a reactor to perform the reaction; the reaction contact time is 16 seconds and the reaction pressure is 0.4 MPa. The reaction temperatures are controlled at 300° C., 350° C., 400° C., and 450° C., respectively. The effluents from the reactors are passed through water to wash away water soluble components and then analyzed with GC-MS. The results of the analyses are shown in Table 1 below:

TABLE 1

Effects of Different Reaction Temperatures

| Reactor Temperature | HCFC-1233xf Conversion Rate | Product Selectivity | | | |
|---|---|---|---|---|---|
| | | HFO-1234yf | HCFC-245cb | HFC-244bb | Others |
| 300° C. | 40.3% | 93.4% | 2.57% | 0.64% | 0.1% |
| 350° C. | 48% | 85.6% | 3.81% | 0.23% | 0.1% |
| 400° C. | 65% | 83% | 3.23% | 0.95% | 0.1% |
| 450° C. | 10.3 | 82.3% | 3.15 | 0.45% | 14.1% |

Example 3

Preparation of HFO-1234yf

In a Monel alloy tube (25 mm diameter), fill with the fluorinated catalyst prepared in Example 1. The amount of the catalyst filled in the tube is 50 ml. Preheat a mixture of anhydrous HF, HCFC-1233xf, and $O_2$ (in different molar ratios) in the preheating can to a temperature of 300° C. Then, introduce the preheated mixture into a reactor to perform the reaction; the reaction temperature is 400° C.; the reaction pressure is 0.4 MPa and the reaction contact time is 16 seconds. The effluents from the reactors are passed through water to wash away water soluble components and then analyzed with GC-MS. The results of the analyses are shown in Table 2 below:

TABLE 2

Effects of Different Ratios of Reaction Materials

| Molar Ratios of Reaction Materials (HF:1233xf:$O_2$) | 1233xf Conversion rate | Product Selectivity | | |
|---|---|---|---|---|
| | | HFO-1234yf | HCFC-245cb | HFC-244bb |
| 3:1:1 | 0.93% | 97.12% | 2.30% | 0.58% |
| 6:1:1 | 4.51% | 95.95% | 3.81% | 0.24% |
| 9:1:1 | 27.60% | 90.46% | 9.15% | 0.39% |
| 12:1:1 | 42.32% | 83.26% | 16.34% | 0.40% |
| 15:1:1 | 65.21% | 81.66% | 19.89% | 0.45% |
| 18:1:1 | 67.2% | 77.54% | 22.10% | 0.36% |

Example 4

Preparation of HFO-1234yf

In a Monel alloy tube (25 mm diameter), fill with the fluorinated catalyst prepared in Example 1. The amount of the catalyst filled in the tube is 50 ml. Preheat a mixture of anhydrous HF, HCFC-1233xf, and $O_2$ (molar ratio 15:1:1) in the preheating can to gasify the mixture at a temperature of 300° C. Then, introduce the preheated mixture into a reactor to perform the reaction; the reaction pressure is 0.4 MPa; the reaction temperature is 400° C.; and the reaction contact times are varied. The effluents from the reactors are passed through water to wash away water soluble components and then analyzed with GC-MS. The results of the analyses are shown in Table 3 below:

TABLE 3

Effects of Different Reaction Contact Times

| Contact Time (s) | 1233xf Conversion Rate | Product Selectivity | | |
|---|---|---|---|---|
| | | HFO-1234yf | HCFC-245cb | HFC-244bb |
| 4 | 3.28% | 95.12% | 4.30% | 0.51% |
| 8.3 | 32.45% | 90.26% | 19.30% | 0.40% |
| 12 | 41.02% | 89.36% | 20.05% | 0.49% |
| 16 | 65.21% | 81.66% | 16.89% | 0.45% |
| 20 | 66.5% | 79.06% | 29.59% | 0.35% |
| 24 | 66.8% | 77.64% | 232.0% | 0.36% |

Example 5

Preparation of HFO-1234yf

In a Monel alloy tube (25 mm diameter), fill with the fluorinated catalyst prepared in Example 1. The amount of the catalyst filled in the tube is 50 ml. Preheat a mixture of anhydrous HF, HCFC-1233xf, and $O_2$ in the preheating can to gasify the mixture at a temperature of 300° C. The molar ratio of anhydrous HF and HCFC-1233xf is kept at 15:1, while the amount of $O_2$ added is varied. Then, introduce the preheated mixture into a reactor to perform the reaction; the reaction pressure is 0.4 MPa; the reaction temperature is 400° C.; and the reaction contact time is 16 seconds. The effluents from the reactors are passed through water to wash away water soluble components and then analyzed with GC-MS. The results of the analyses are shown in Table 4 below:

TABLE 4

Effects of Different Amounts of Oxygen

| Molar Ratios of Reaction Material (HF:1233xf:$O_2$) | 1233xf Conversion Rate | Product Selectivity | | |
|---|---|---|---|---|
| | | HFO-1234yf | HCFC-245cb | HFC-244bb |
| 15:1:0 | 10.31% | 93.26% | 6.19% | 0.45% |
| 15:1:1 | 65.21% | 81.66% | 16.89% | 0.45% |
| 15:1:1.5 | 66.31% | 81.02% | 16.88% | 0.44% |
| 15:1:2 | 67.60% | 80.76% | 16.85% | 0.48% |
| 15:1:2.5 | 67.87% | 80.16% | 16.88% | 0.45% |
| 15:1:3 | 68.21% | 79.56% | 16.87% | 0.46% |

Example 6

Preparation of HFO-1234yf

In a Monel alloy tube (25 mm diameter), fill with the fluorinated catalyst prepared in Example 1. The amount of the catalyst filled in the tube is 50 ml. Preheat a mixture of anhydrous HF, HCFC-1233xf, and $O_3$ in the preheating can to gasify the mixture at a temperature of 300° C. The molar ratio of anhydrous HF and HCFC-1233xf is kept at 15:1, while the amount of $O_3$ added is varied. Then, introduce the preheated mixture into a reactor to perform the reaction; the reaction pressure is 0.4 MPa; the reaction temperature is 400° C.; and the reaction contact time is 16 seconds. The effluents from the reactors are passed through water to wash away water soluble components and then analyzed with GC-MS. The results of the analyses are shown in Table 5 below:

TABLE 5

Comparison of Different Amounts of $O_3$

| Molar Ratios of Reaction Material (HF:1233xf:$O_3$) | 1233xf Conversion Rate | Product Selectivity | | |
|---|---|---|---|---|
| | | HFO-1234yf | HCFC-245cb | HFC-244bb |
| 15:1:0 | 10.31% | 93.26% | 6.19% | 0.45% |
| 15:1:0.2 | 25.35% | 90.66% | 8.29% | 0.45% |
| 15:1:0..5 | 46.31% | 85.02% | 13.88% | 0.44% |
| 15:1:0.8 | 68.60% | 80.76% | 17.85% | 0.48% |
| 15:1:1.0 | 69.30% | 75.26% | 22.68% | 0.45% |
| 15:1:1.5 | 69.61% | 74.46% | 22.67% | 0.46% |
| 15:1:2.0 | 69.81% | 70.86% | 25.7% | 0.46% |

Example 7

Preparation of HFO-1234yf

Prepare fluorination catalysts according to the procedures of Example 1, with the following variations:
(1) Fluorination catalyst 2: replace chromium nitrate with chromium chloride;
(2) Fluorination catalyst 3: replace lanthanum nitrate with cerium nitrate;
(3) Fluorination catalyst 4: replace lanthanum nitrate with praseodymium nitrate;
(4) Fluorination catalyst 5: add 0.1% (wt) of perfluoro-1-octanesulfonyl fluoride (POSF) into the mixed slat solution.

In a Monel alloy tube (25 mm diameter), fill with the fluorinated catalyst 1-5. The amount of the catalyst filled in the tube is 50 ml. Preheat a mixture of anhydrous HF, HCFC-1233xf, and $O_2$ in the preheating can to gasify the mixture at a temperature of 300° C. The molar ratio of anhydrous HF and HCFC-1233xf is kept at 15:1, while the amount of $O_2$ added is varied. Then, introduce the preheated mixture into a reactor to perform the reaction; the reaction pressure is 0.4 MPa; the reaction temperature is 400° C.; and the reaction contact time is 16 seconds. The effluents from the reactors are passed through water to wash away water soluble components and then analyzed with GC-MS. The results of the analyses are shown in Table 6 below:

TABLE 6

Effects of Different Rare Earth Metals

| Catalyst | 1233xf Conversion Rate | HFO-1234yf | HFC-245cb | HCFC-244bb |
|---|---|---|---|---|
| Fluorination Catalyst 1 | 65.21% | 81.66% | 17.59% | 0.45% |
| Fluorination Catalyst 2 | 67.35% | 86.66% | 12.19% | 0.45% |
| Fluorination Catalyst 3 | 64.32% | 83.12% | 15.88% | 0.44% |
| Fluorination Catalyst 4 | 65.30% | 84.76% | 14.15% | 0.48% |
| Fluorination Catalyst 5 | 68.36% | 87.26% | 11.89% | 0.45% |

*Note:
other impurities are present in very low amounts and are not listed.

Example 8

Preparation of Catalysts

Prepare and process different fluorination catalysts according to the procedures of Example 1, with the following variations:
(1) Fluorination catalyst 6 (Molar Ratio, Cr:Al=1:0.005): remove $La(NO_3)_3.6H_2O$, and replace with 3 g $Al(NO_3)_3.9H_2O$;
(2) Fluorination catalyst 7 (Molar Ratio, Cr:La=1:0.30): increase the amount of $La(NO_3)_3.6H_2O$ from 0.32 g to 19.4 g;
(3) Fluorination catalyst 8: add 0.3% (wt) of perfluoro-1-octanesulfonyl fluoride (POSF) into the mixed slat solution for fluorination catalyst 7;

Example 9

Preparation of HFO-1234yf

In a Monel alloy tube (25 mm diameter), fill with the fluorinated catalyst 6, 7, 8, or 9. The amount of the catalyst filled in the tube is 50 ml. Preheat a mixture of anhydrous HF, HCFC-1233xf, and $O_2$ in the preheating can at a temperature of 300° C. The molar ratio of anhydrous HF and HCFC-1233xf is kept at 15:1, while the amount of $O_2$ added is varied. Then, introduce the preheated mixture into a reactor to perform the reaction; the reaction pressure is 0.4 MPa; the reaction temperature is 400° C.; and the reaction contact time is 16 seconds. The effluents from the reactors are passed through water to wash away water soluble components and then analyzed with GC-MS. The results of the catalyst lives analyses are shown in Table 7 below:

Reaction 1: Catalyst 6, HF:HCFC-1233xf:$O_2$=15:1:0.5;

Reaction 2: Catalyst 1, HF:HCFC-1233xf:$O_2$=15:1:1;

Reaction 3: Catalyst 7, HF:HCFC-1233xf:$O_2$=15:1:1;

Reaction 4: Catalyst 8, HF:HCFC-1233xf:$O_2$=15:1:1;

Reaction 5: Catalyst 1, HF:HCFC-1233xf:$O_2$=15:1:0.5;

TABLE 7

Catalyst Life Evaluation

| Duration | Components | | Rxn 1 | Rxn 2 | Rxn 3 | Rxn 4 | Rxn 5 |
|---|---|---|---|---|---|---|---|
| 50 hrs | 1233xf Conversion | | 36.89% | 65.23% | 59.39% | 68.37% | 67.58% |
| | Selectivity | HFO-1234yf | 75.26% | 81.68% | 81.25% | 83.18% | 82.98% |
| | | HFC-245cb | 23.95% | 17.38% | 17.75% | 15.80% | 15.95% |
| | | HCFC-244bb | 0.48% | 0.45% | 0.46% | 0.50% | 0.54% |
| 100 hrs | 1233xf Conversion | | 30.90% | 63.78% | 57.28% | 65.31% | 65.07% |
| | Selectivity | HFO-1234yf | 73.62% | 80.78% | 80.75% | 82.79% | 81.99% |
| | | HFC-245cb | 24.35% | 17.95% | 18.05% | 15.99% | 16.65% |
| | | HCFC-244bb | 1.51% | 0.75% | 0.73% | 0.71% | 0.80% |
| 200 hrs | 1233xf Conversion | | 28.85% | 60.46% | 54.49% | 62.41% | 62.10% |
| | Selectivity | HFO-1234yf | 70.05% | 78.59% | 78.25% | 79.94% | 79.64% |
| | | HFC-245cb | 25.48% | 18.85% | 19.15% | 17.64% | 17.84% |
| | | HCFC-244bb | 4.99% | 2.09% | 2.17% | 1.94% | 2.03% |
| 300 hrs | 1233xf Conversion | | 25.34% | 57.68% | 51.24% | 59.51% | 59.03% |
| | Selectivity | HFO-1234yf | 66.38% | 75.61% | 75.17% | 76.89% | 76.24%. |
| | | HFC-245cb | 26.12% | 20.26% | 20.36% | 19.36% | 19.84% |
| | | HCFC-244bb | 6.60% | 3.34% | 3.69% | 3.02% | 3.14% |

*Note:
other impurities are present in very low amounts and are not listed.

What is claimed is:

1. A fluorination catalyst for preparing 2,3,3,3-tetrafluoropropene, characterized in that the fluorination catalyst has the following formula (I):

$$Cr_1(Y,Z)_{0.005-0.5}O_{0.1-1.0}F_{1.0-3.0} \quad (I)$$

wherein Y is selected from Al, Zn, Mg, or a combination thereof, and Z is a rare earth element that is capable of storing and releasing oxygen and is selected from Ce, La, Pr, or a combination thereof.

2. The fluorination catalyst for preparing 2,3,3,3-tetrafluoropropene according to claim 1, characterized in that the fluorination catalyst was prepared by a process, in which a fluorine-containing surfactant was added.

3. The fluorination catalyst for preparing 2,3,3,3-tetrafluoropropene according to claim 2, characterized in that the fluorine-containing surfactant is perfluorooctylsulfonyl fluoride or a soluble salt of perfluorooctylsulfonic acid.

4. A method for preparing 2,3,3,3-tetrafluoropropene, comprising: reacting 2-chloro-3,3,3-trifluoropropene as a starting material with anhydrous hydrogen fluoride, under catalysis of the fluorination catalyst of claim 1 and in the presence of O₂ and/or O₃, to produce 2,3,3,3-tetrafluoropropene.

5. The method for preparing 2,3,3,3-tetrafluoropropene according to claim 4, characterized in that the rare earth element is selected from Ce, La, Pr, or a combination thereof.

6. The method for preparing 2,3,3,3-tetrafluoropropene according to claim 4, characterized in that the fluorine-containing surfactant is perfluorooctylsulfonyl fluoride or a soluble salt of perfluorooctylsulfonate.

7. The method for preparing 2,3,3,3-tetrafluoropropene according to claim 4, characterized in that a molar ratio of the anhydrous hydrogen fluoride and 2-chloro-3,3,3-trifluoropropene is 3-20:1.

8. The method for preparing 2,3,3,3-tetrafluoropropene according to claim 7, characterized in that the molar ratio of the anhydrous hydrogen fluoride and 2-chloro-3,3,3-trifluoropropene is 5-10:1.

9. The method for preparing 2,3,3,3-tetrafluoropropene according to claim 4, characterized in that reaction is conducted in the presence of O₂, wherein a molar ratio of O₂ and 2-chloro-3,3,3-trifluoropropene is 1-3:1.

10. The method for preparing 2,3,3,3-tetrafluoropropene according to claim 9, characterized in that reaction is conducted in the presence of O₂, wherein the molar ratio of O₂ and 2-chloro-3,3,3-trifluoropropene is 1-2:1.

11. The method for preparing 2,3,3,3-tetrafluoropropene according to claim 4, characterized in that reaction is conducted in the presence of O₃, wherein a molar ratio of O₃ and 2-chloro-3,3,3-trifluoropropene is 0.1-2:1.

12. The method for preparing 2,3,3,3-tetrafluoropropene according to claim 11, characterized in that reaction is conducted in the presence of O₃, wherein the molar ratio of O₃ and 2-chloro-3,3,3-trifluoropropene is 0.1-1:1.

13. The method for preparing 2,3,3,3-tetrafluoropropene according to claim 4, characterized in that a reaction temperature is in a range of 200-500° C. and a reaction contact time is in a range of 1-300 seconds.

14. The method for preparing 2,3,3,3,-tetrafluoropropene according to claim 13, characterized in that the reaction temperature is in a range of 300-450° C. and the reaction contact time is in a range of 5-25 seconds, and wherein a reaction pressure is in a range of 0.1-1.2 MPa.

15. The method for preparing 2,3,3,3,-tetrafluoropropene according to claim 4, characterized in that 2-chloro-3,3,3-trifluoropropene as the starting material is preheated prior to reaction, and a preheating temperature is in a range of 100-350° C.

16. A method for preparing 2,3,3,3-tetrafluoropropene, characterized in that the method comprises the following steps:
(1) introducing the fluorination catalyst according to claim 1 into a reactor;
(2) introducing into the reactor a gasified and preheated mixture of starting material 2-chloro-3,3,3-trifluoropropene, anhydrous hydrogen fluoride, and O₂ and/or O₃ to effect a reaction, wherein the mixture was preheated at a preheating temperature in a range of 100-500° C., and a reaction temperature is in a range of 300-450° C.;
(3) introducing a reaction product stream into a first separation tower, and separating from a top of the first separation tower a stream of O₂ and/or O₃ and HCl, which is passed through water to remove HCl and remaining O₂ and/or O₃ is let out into atmosphere or passed through a device for recovery, and isolating, from a pot in the first separation tower, a stream containing HCFC-1233xf, HFO-1234yf and HF, which is introduced into a second separation tower for further separation;

(4) separating from the second separation tower a stream containing crude HFO-1234yf, which is purified to produce a final product; and (5) returning a stream remaining at a bottom of the second separation tower into the reactor to continue the reaction.

17. The method for preparing 2,3,3,3-tetrafluoropropene according to claim 16, characterized in that the fluorination catalyst was prepared by a process, in which a fluorine-containing surfactant was added, and wherein the fluorination catalyst is pretreated with HF at a temperature in a range of 200-500° C. for 15-400 minutes prior to use.

18. The method for preparing 2,3,3,3-tetrafluoropropene according to claim 16, characterized in that a molar ratio of the anhydrous hydrogen fluoride and 2-chloro-3,3,3-trifluoropropene is 5-10:1.

* * * * *